United States Patent [19]

Komiya

[11] 4,249,533
[45] Feb. 10, 1981

[54] LASER KNIFE

[75] Inventor: Osamu Komiya, Hachioji, Japan

[73] Assignee: Olympus Optical Co., Ltd., Tokyo, Japan

[21] Appl. No.: 902,864

[22] Filed: May 4, 1978

[30] Foreign Application Priority Data

May 16, 1977 [JP] Japan ............................ 52/62823[U]
Jun. 21, 1977 [JP] Japan .................................. 52/73713

[51] Int. Cl.³ ............................................... A61B 17/36
[52] U.S. Cl. ................................ 128/303.1; 128/321; 128/395
[58] Field of Search ................. 128/303.1, 395, 305, 128/3, 4, 5, 6, 7, 8, 634, 321, 303 A, 325, 303.13–303.18, 328

[56] References Cited

U.S. PATENT DOCUMENTS

| | | | |
|---|---|---|---|
| 2,114,695 | 4/1938 | Anderson | 128/321 |
| 2,670,519 | 3/1954 | Recklitis | 128/321 |
| 3,074,408 | 1/1963 | Chester | 128/328 |
| 3,417,746 | 12/1968 | Moore et al. | 128/6 |
| 3,821,510 | 6/1974 | Muncheryan | 128/303.1 |
| 3,865,113 | 2/1975 | Sharon et al. | 128/303.1 |
| 3,924,608 | 12/1975 | Mitsui | 128/6 |
| 4,011,872 | 3/1977 | Komiya | 128/303.1 |
| 4,027,510 | 6/1977 | Hiltebrandt | 128/6 |
| 4,072,147 | 2/1978 | Hett | 128/303.1 |
| 4,085,743 | 4/1978 | Yoon | 128/6 |

FOREIGN PATENT DOCUMENTS 2412690 10/1974 Fed. Rep. of Germany .......... 128/328

Primary Examiner—Robert W. Michell
Assistant Examiner—Arthur S. Rose
Attorney, Agent, or Firm—Weinstein & Sutton

[57] ABSTRACT

A laser knife comprises a tubular member adapted to be passed through a forceps channel of an endoscope for insertion into a coeloma, holders disposed at the distal end of the tubular member for holding an affected part within the coeloma which is to be cauterized, a laser radiation transmission member for irradiating the affected part held by the holders with radiation from a laser, and a pad on the holders for accepting the laser radiation subsequent to the completion of the cautery, thus preventing the irradiation of normal tissues with the laser radiation.

22 Claims, 15 Drawing Figures

[4,249,533]

LASER KNIFE

BACKGROUND OF THE INVENTION

The invention relates to a laser knife, and more particularly to a laser knife which is utilized to cauterize the tissues of an affected part within the coeloma with laser radiation for excision or coagulation purposes.

The incision or excision of an affected part within the coeloma such as a polyp has heretofore been achieved by the use of excision scissors or an incision knife which is passed through the forceps channel of a flexible tube of an endoscope so as to move out of and into the distal end of the tube. However, such technique requires a high level of skill and is also time consuming. The operation is even more burdensome due to the need for stanching, sterilization and like treatment.

There has been an attempt to achieve such incision or excision of an affected part through the use of laser radiation which is directed thereto for cautery of the affected part. This will eliminate the need for the stanching or sterilization. However, the very high intensity of laser radiation may cause an unintended irradiation and cautery of normal tissues or even a piercing thereof with laser radiation after the latter has cauterized the intended part.

SUMMARY OF THE INVENTION

It is an object of the invention to provide a laser knife which eliminates the described disadvantages of the prior art by the use of laser radiation, which is enabled by a laser radiation pad mounted on holders which secure an intended affected part in position and which prevent the laser radiation from irradiating other parts of a physical body after it has cauterized the intended part.

With the laser knife of the invention, the tissues of an affected part can be cauterized by the laser radiation for incision, excision or coagulation, thus removing the need of stanching and sterilization. As a consequence, the surgery can be simply achieved within a reduced length of time. The provision of the laser radiation pad avoids the need for the skill of an operator, assuring a safe operation. The intensity of the laser radiation can be adjusted to a lower level for cautery of a salpinx for purpose of contraception. In this manner, the applicability of the laser knife can be extended for improving its practical utility.

DESCRIPTION OF PREFERRED EMBODIMENTS

Figure 1:
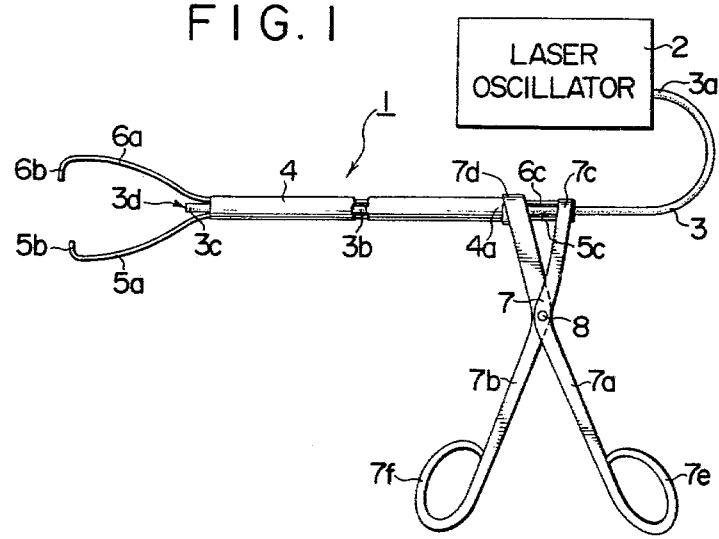
FIG. 1 is a side elevation of a laser knife according to one embodiment of the invention.
Figure 2:
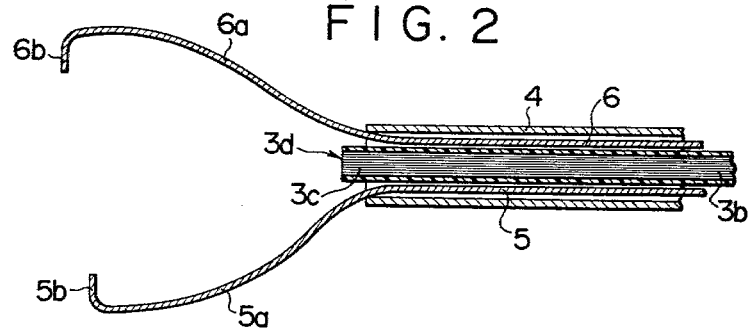
FIG. 2 is a fragmentary enlarged cross section of the holders shown in FIG. 1.
Figure 3:
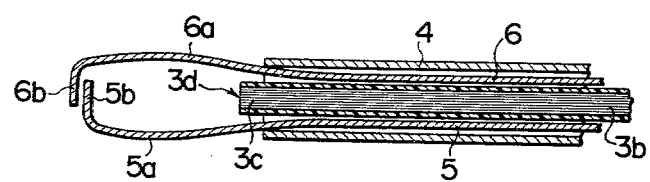
FIG. 3 is a fragmentary enlarged cross section of the holders when they are closed.

Referring to FIG. 1, there is shown a side elevation of laser knife 1 constructed according to one embodiment of the invention. Radiation produced by a laser oscillator 2 is introduced into laser radiation transmission member 3 for purpose of cautery of an affected part. The transmission member 3 may comprise a bundle of optical fibers, which have their one end 3a detachably coupled with the oscillator 2. As shown in FIG. 2, the free length 3b of the transmission member is passed through a flexible, tubular member 4 which is adapted to be inserted into the coeloma, with its distal end 3c projecting forwardly from the distal end of the tubular member 4. The end face of the distal end 3c is formed as a laser radiation emitting area 3d for irradiating an affected part to be cauterized with the laser radiation fed through the transmission member 3.

A pair of holding members 5, 6 freely extend through the tubular member. The holding members 5, 6 are in the form of elongate resilient strips, and are disposed diametrically opposite to each other in surrounding relationship with the transmission member 3. The distal end of the members 5, 6 project forwardly from the distal end of the tubular member 4 forming holders 5a, 6a which are adapted to hold an affected part sandwiched therebetween. It is to be noted that the holders 5a, 6a which extend out of the distal end of the tubular member 4 are resiliently biased apart. The extremity of each holder is bent inwardly toward the other to form a laser radiation pad 5b, 6b. As shown in FIG. 1, the opposite ends 5c, 6c of the holding members 5, 6 extend out of the tubular member 4 and are connected with an operating member 7.

The operating member 7 is scissor-shaped, comprising a pair of chevron-shaped arms 7a, 7b. The arms 7a, 7b are pivotally connected together by a pin 8 which is located at the apex of each of the respective chevrons. The ends 5c, 6c of the holding members are fixedly connected with one end 7c of the arm 7a, and the end 4a of the tubular member 4 is fixedly connected with one end 7d of the arm 7b. The opposite ends of both arms 7a, 7b are formed with loops 7e, 7f so as to receive a pair of fingers therein. While the overall configuration of the operating member 7 is scissor-like, it operates in the opposite manner from that of the usual scissors. Namely, when the fingers are inserted into the loops 7e, 7f to move them toward each other, the arm ends 7c, 7d move away each other. Thereupon, the end 7c acts to draw the holding members 5, 6 into the tubular member 4 while the end 7d tends to move the tubular member 4 in the opposite direction, so that the holders 5a, 6a are moved toward each other against their own resilience until the pads 5b, 6b are brought into overlapping relationship with each other and are located forwardly of and in opposing relationship with the emitting area 3d of the transmission member 3.

Figure 4:
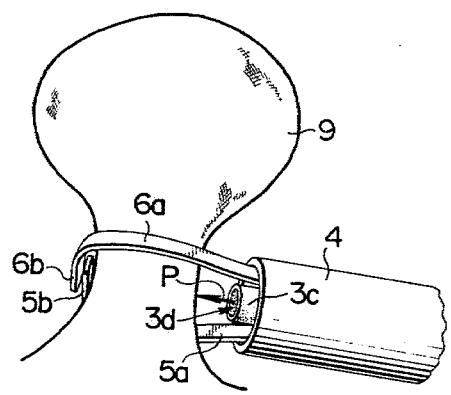
FIG. 4 is a perspective view illustrating the use of the laser knife for the excision of a polyp within the coeloma.

When the laser knife 1 is used to excise the tissues of an affected part such as polyp located in the coeloma, the tubular member 4 is passed into the forceps channel of an endoscope, of either the direct or lateral view type, and the distal end of the tubular member 4, holders 5a, 6a and the emitting area 3d are allowed to extend from the inner end of the endoscope. While observing the sight obtained through the endoscope, the distal end of the tubular member 4 is extended out of the endoscope and manipulated so that the polyp can be surrounded by the holders 5a, 6a. Subsequently, the operating member 7 is operated in the manner mentioned above to hold polyp 9 sandwiched between the holders 5a, 6a as shown in FIG. 4. The laser radiation emitting area 3d is directed toward an intended region such as the neck of polyp 9, which is to be cauterized with the laser radiation. Thereafter the laser radiation from the oscillator 2 can be fed into the transmission member 3. Thereupon, the tissues of the affected part are cauterized by irradiation with the laser radiation, and polyp 9 can be excised within a short period of time. After polyp 9 is excised, laser radiation P will be directed toward the pads 5b, 6b, thus preventing the likelihood of irradiating normal tissues with the laser radiation. In this manner, the surgery of an affected part can be achieved in a safe manner using the laser knife 1 of the invention.

Figure 5:
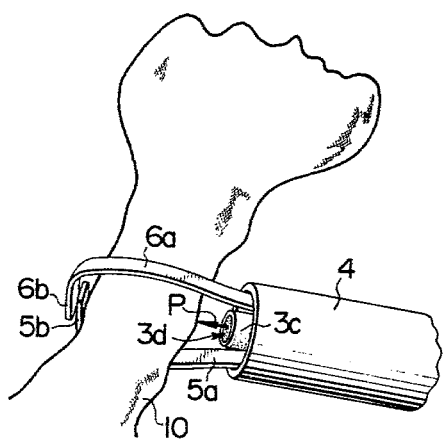
FIG. 5 is a perspective view illustrating the use of the laser knife for cautery of a salpinx.

FIG. 5 illustrates the cautery of a salpinx 10 with the laser knife 1 for purpose of contraception. The intensity of laser radiation which is required for the cautery of the salpinx 10 is reduced as compared with that which is necessary to perform the excision.

Figure 6:
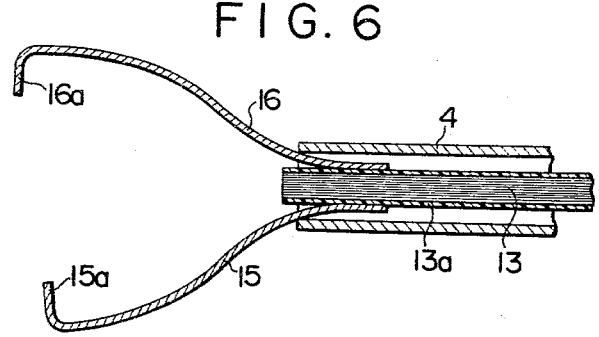
FIG. 6 is a fragmentary enlarged cross section of another example of holders.

FIG. 6 is a fragmentary view of another embodiment of the invention. In this instance, a laser radiation transmission member 13 comprises a bundle of optical fibres which are contained within an outer sleeve 13a, to which a pair of holding members 15, 16 are directly attached at one of their ends. The sleeve 13a is connected with an operating member as shown at 7 in FIG. 1. As a consequence, the transmission member 13 moves integrally with the holding members 15, 16 inside the tubular member 4 for opening or closing holders 15a, 16a.

Figure 7:
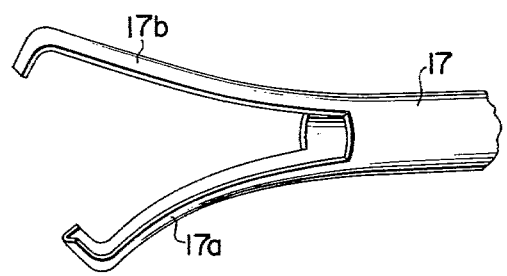
FIG. 7 is a fragmentary perspective view of a further example of holders.

FIG. 7 shows another example of the holding member. In this instance, a holding member 17 comprises a hollow cylindrical body, the inner end of which is notched to form a pair of holders 17a, 17b. These holders are also resiliently biased part, and have their inner ends folded inwardly toward each other to form radiation pads. The holding members 15, 16, 17 shown in FIGS. 6 and 7 reduce the number of parts required for constructing the laser knife 1, enabling a reduction in the manufacturing cost and assuring a stable operation.

Figure 8:
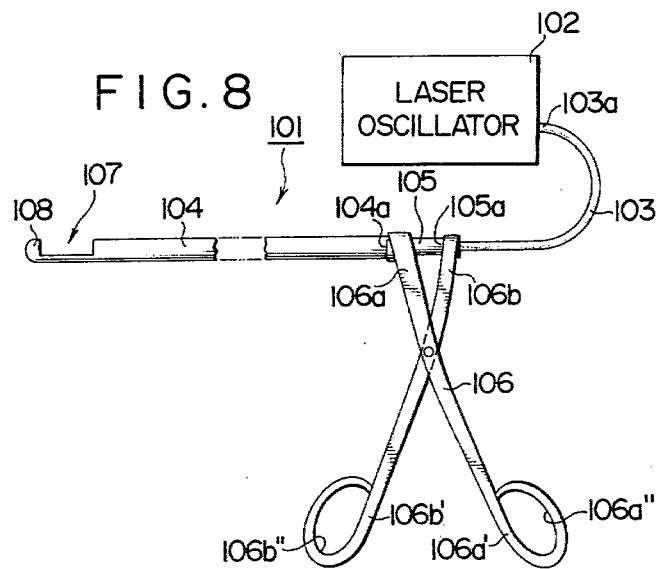
FIG. 8 is a side elevation of a laser knife constructed according to another embodiment of the invention.
Figure 9:
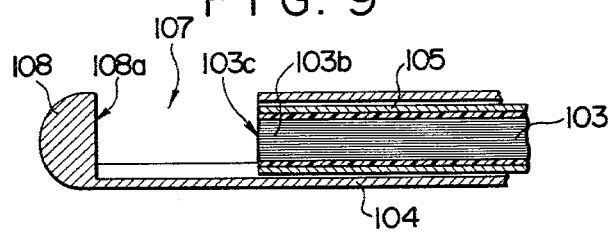
FIG. 9 is a fragmentary enlarged cross section of the holders shown in FIG. 8.

FIG. 8 is a side elevation of laser knife 101 which is constructed according to a further embodiment of the invention. Laser radiation from an oscillator 102 is introduced into a radiation transmission member 103 for the cautery of an affected part. The transmission member 103 again comprises a bundle of optical fibres, and has its one end 103a detachably coupled with the oscillator 102. The free length of the transmission member 103 extends through a flexible holding member 105, with its opposite end 103b located at the distal end of the holding member 105 to form a laser radiation emitting area 103c, as shown in FIG. 9. The laser radiation can be directed toward an affected part to be cauterized from the emitting area 103c. It is to be noted that the emitting area 103c also serves as one of holders which are used to hold an affected part together with its mating holder. The holding member 105 freely extends through a tubular member 104, and the distal end 108 of the latter is shaped as a hemi-spherical body to provide a notch or recess 107 between it and the emitting area 103c which is adpated to receive the part to be cauterized. The distal end 108 is provided with a radiation pad 108a.

The proximate ends 104a, 105a of the tubular member 104 and holding member 105 are fixedly connected with one end of a pair of arms 106a, 106b of a scissors-like operating member 106. The arms 106a, 106 b are pivotally connected together intermediate their ends, and their opposite ends 106a', 106b' are formed with loops 106a'', 106b'' which are adapted to receive the operator's fingers therein. When the fingers are inserted into the loops to move the loops toward each other, the ends of the arms which are connected with the tubular member 104 and the holding member 105 also move toward each other, so that the tubular member 104 moves to the right while the holding member 105 moves in the opposite direction, whereby its distal end projects forwardly from the tubular member 104.

Figure 10:
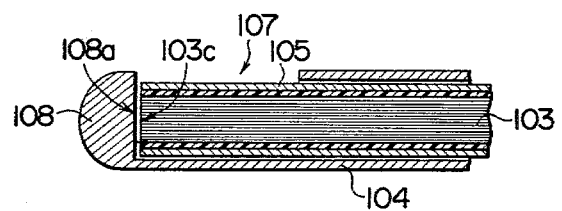
FIG. 10 is a fragmentary enlarged cross section of the holders shown in FIG. 9 when they are closed.

In the condition shown in FIG. 8, namely, when the scissors are open, the emitting area 103c is spaced from the pad surface 108a as shown in FIG. 9. However, when the scissors are closed, the emitting area 103c moves forward into the recess 107 until it bears against the pad surface 108a at the distal end of the tubular member 104, as shown in FIG. 10.

Figure 11:
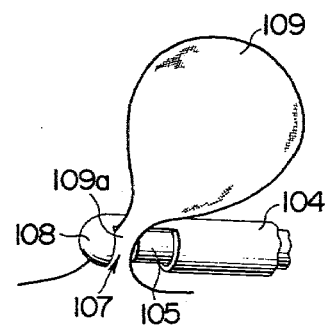
FIG. 11 is a perspective view illustrating the use of the laser knife shown in FIG. 8 for the excision of a polyp located within the coeloma.

When the laser knife 1 is used for excision of the tissues of an affected part such as a polyp located within the coeloma, the tubular member 104 is inserted into the forceps channel of an endoscope as shown in FIG. 9, and while observing the view created by the endoscope, the operating member 106 is operated in a manner such that a base 109a of polyp 109 is held sandwiched between the pad surface 108a and the emitting area 103c, as shown in FIG. 11. Thereafter the oscillator 102 may be turned on to irradiate the polyp with the laser radiation. When irradiated in this manner, the base 109a of the polyp will be cauterized in a reduced time, thus allowing the excision of polyp 109. After the excision of polyp 109, laser radiation will be directed toward the pad 108a, thus avoiding any likelihood of normal tissues within the coeloma being inadvertently irradiated with the laser radiation. Thus the surgery of an affected part can be achieved in a simple and safe manner within a reduced time while avoiding any risk which may result from the use of laser radiation.

Figure 12:
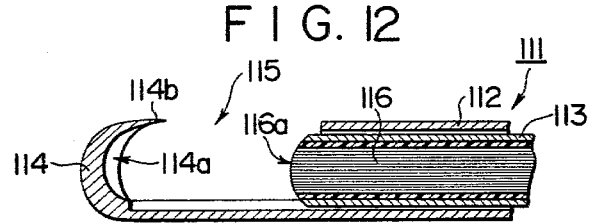
FIG. 12 is a fragmentary enlarged cross section of a laser knife according to a further embodiment of the invention.

FIG. 12 shows a modified laser knife 11 which is preferred for use for the contraception surgery. In this embodiment, the laser knife 111 is similar in construction to the embodiment shown in FIGS. 8 to 10 except for the holder arrangement. Accordingly, corresponding parts are designed by like numerals without repeating their description. The laser knife 111 includes a tubular member 112, which is formed with a radiation pad 114 which is of a crescent form in section and which also serves as one of the holders. At its top end, as viewed in FIG. 12, the pad 114 is formed with an acicular projection 114b which extends toward a recess 115 which is adapted to receive an affected part therein. A holding member 113 contains laser radiation transmission member 116 which is formed with an emitting area 116a at its one end, the emitting area serving as the other holder and being formed as a spherical surface in conformity to the configuration of the pad surface 114a.

Figure 13:
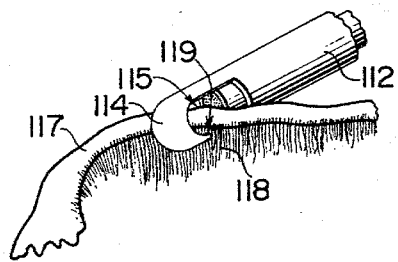
FIG. 13 is a fragmentary perspective view of the laser knife of FIG. 12 illustrating its use for the cautery of a salpinx.

For surgery of contraception, it is usually sufficient to coagulate, rather than excise, the salpinx. Referring to FIG. 13, salpinx 117 is shown located in the recess 115. By operating the scissor-like operating member (refer to FIG. 8), an opening 119 is pierced, through chorial tissue 118 by the acicular projection 114b, and salpinx 117 is held sandwiched between the pad 114a and the emitting surface 116a. In this manner, no special independent means for piercing the opening 119 or holding the salpinx 117 is required, thus facilitating the contraception operation.

Figure 14:
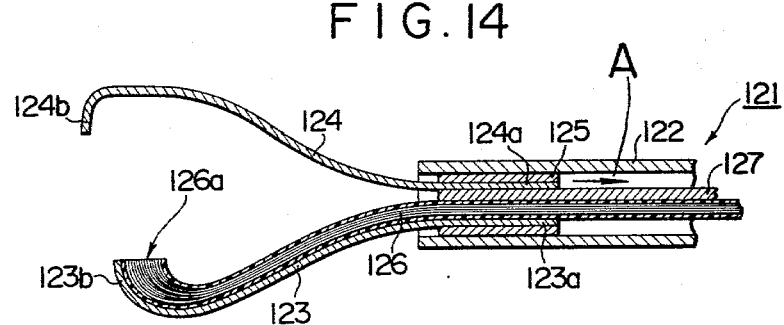
FIG. 14 is a fragmentary enlarged cross section of the holders of a laser knife constructed according to a further embodiment of the invention.
Figure 15:
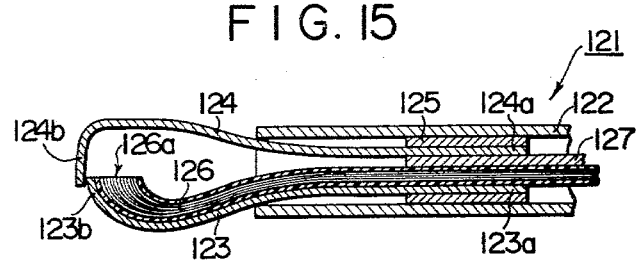
FIG. 15 is an enlarged cross section of the holders of FIG. 14 in their closed position.

FIGS. 14 and 15 show another embodiment of the invention in which during the opening and closing, the holders move in a direction perpendicular to the lengthwise direction rather than moving in the lengthwise direction of the tubular member as in the previous embodiments of FIGS. 8-13. A laser knife 121 includes a tubular member 122, and a pair of holders 123, 124 each having one end secured to a cylindrical holding member 125 which is freely movable inside the tubular member 122. One of the holders, 123, comprises an elongated resilient strip having its distal end 123b shaped like a spoon. The other end 123a of the holder 123 is fixedly connected with the holding member 125.

A laser radiation transmission member 126 is supported by the holding member 125 and extends forwardly along the holder 123, with its laser radiation emitting area 126a located at the distal end 123b of the holder 123 and directed toward the other holder 124. The opposite end, not shown, of the transmission member 126 is connected with a laser oscillator (refer to FIG. 8) after passing through the tubular member 122. The distal end 124b of the other holder 124 extends slightly beyond the distal end 123b of the holder 123, and is shaped in the form of a lid which can cover the distal end 123b when the holders are brought together. The holder 124 also comprises an elongated resilient strip, with its opposite end 124a fixedly connected with the holding member 125. Both holders are resiliently biased apart but can be closed against each other as shown in FIG. 15 by moving them in the direction of arrow a with an operating rod 127 which is connected thereto. This movement can be achieved by using a scissors-like operating member as shown in FIG. 8 which has its arms connected with the proximate ends of the tubular member 122 and the operating rod 127, respectively.

It will be understood that the laser knife 121 can be used in a manner similar to the previous embodiments. Since the holders 123, 124 are adapted to move in a direction perpendicular to the lengthwise direction of the tubular member 122 when they are opened or closed, they can grasp an affected part of a greater volume, thus facilitating the grasping operation.

It is to be noted that an affected part to be treated continues moving within the coeloma, so that a precise treatment of a desired site is difficult when the knife is introduced into the coeloma through the channel of an endoscope. However, with the laser knife of the invention, the desired region of an affected part can be positively held, permitting a reliable and safe treatment. Since the laser knife is used while viewing the affected part through the endoscope, the ease and safety of an operation is assured.

While the laser radiation transmission member has been described as comprising a bundle of optical fibres, it will be understood that any member, such as a glass or plastic rod, liquid fibre, optical lenses, which member is capable of transmitting laser radiation, can be used. The tubular member used in the laser knife of the invention may be flexible whenever the channel of the endoscope used is flexible, or may be inflexible when the endoscope is inflexible.

What is claimed is:

1. A laser knife comprising a tubular member adapted to be inserted into the forceps channel of an endoscope, first means for generating laser radiation sufficient to cauterize tissue, a laser radiation transmission member having a first end and a second end, said laser radiation transmission member being disposed within said tubular member and extending along the length thereof for conveying laser radiation therethrough so that laser radiation derived from said first means is conveyed from said first end of said laser radiation transmission member to be emitted from said second end of said laser radiation transmission member, holding means located at said second end of said laser radiation transmission member for holding an affected part to be cauterized by said emitted laser radiation, said holding means including a pair of opposed holding members which are movable relative to one another; means for moving at least one of said holding members relative to the other between a first position and a second position, said first position adapted to hold said affected part and said second position adapted to release said affected part, and acceptor means being positioned on one of said holding members such that said acceptor means is moved by said one of said holding members to a position disposed in optical alignment with said second end of said laser radiation transmission member when said holding members are moved to said first position from said second position for accepting said laser radiation emitted from said second end of said laser radiation transmission member upon completion of cautery of said affected part to prevent the likelihood of irradiating normal tissue with the laser radiation.

2. The laser knife of claim 1 wherein said one of said holding members includes an end portion and said acceptor means comprises a laser radiation pad formed at said end portion.

3. The laser knife of claim 1 wherein said holding means is axially movable within said tubular member between said first and second positions, said holding members comprising first and second arms resiliently biased apart and being axially movable relative to said tubular member so that when said holding means is axially moved to said first position said tubular member urges said first and second arms towards each other.

4. The laser knife of claim 3 wherein said holding means is mounted on said second end of said laser radiation transmission member, and said laser radiation transmission member is axially movable within said tubular member.

5. The laser knife of claim 3 including retaining means axially movable within said tubular member, said holding means being mounted on said retaining means.

6. The laser knife of claim 3 including operating means for axially moving said holding means within said tubular member, said tubular member urging said first and second arms towards each other against said resilient bias when said holding means moves in a predetermined direction within said tubular member.

7. The laser knife of claim 3 wherein said first and second arms include end portions, and said acceptor means comprises laser radiation pads formed at said ends of said first and second arms.

8. The laser knife of claim 7 wherein said laser radiation pads are formed by inwardly folding said ends of said first and second arms.

9. The laser knife of claim 8 wherein said laser radiation pads substantially overlap each other at a location which is in optical alignment with said second end of said laser radiation transmission member when said first and second arms are holding an affected part.

10. The laser knife of claim 3 wherein said means for moving said opposed members comprises displacing means for axially moving said holding means with respect to said tubular member.

11. The laser knife of claim 10 wherein said displacing means includes a first arm affixed to said tubular member and a second arm affixed to said holding means, said first and second arms being pivotally connected to each other.

12. The laser knife of claim 3 wherein said first arm supports said laser radiation transmission member and said second arm supports said acceptor means.

13. The laser knife of claim 12 wherein the free end of said first arm is bent to extend toward said second arm, the second end of said laser radiation transmission member being supported by the free end of said first arm.

14. The laser knife of claim 1 wherein said holding means is formed from a cylindrical body; said opposed members comprising a pair of arms joined to said cylindrical body at one end thereof.

15. The laser knife of claim 1 wherein said laser radiation transmission means comprises a plurality of fiber optic members.

16. The laser knife of claim 1 wherein one of said holding members comprises retainer means carrying said laser radiation transmission member, said retainer means being axially movable within said tubular member between said first and second positions in said tubular member so that when said holding members are in said first position, said affected part is positioned between said second end of said laser radiation transmission member and said acceptor means.

17. The laser knife of claim 16 wherein said means for moving said opposed members includes / displacing means for axially moving said retainer means with respect to said tubular member.

18. The laser knife of claim 17 wherein said displacing means includes a first arm affixed to said tubular member and a second arm affixed to said retainer means, said first and second arms being pivotally connected to each other.

19. The laser knife of claim 16 wherein said retainer means also carries said acceptor means.

20. The laser knife of claim 16 wherein said second end of said laser radiation transmission member and said acceptor means include correspondingly mating surfaces.

21. The laser knife of claim 20 wherein said correspondingly mating surfaces comprise convex and concave surfaces.

22. The laser knife of claim 1 wherein said acceptor means comprises a planar surface which is disposed substantially parallel to said second end of said laser radiation transmission means when said holding means is in said first position holding an affected part.

* * * * *

UNITED STATES PATENT AND TRADEMARK OFFICE
CERTIFICATE OF CORRECTION

PATENT NO. : 4,249,533
DATED : February 10, 1981
INVENTOR(S) : Osamu Komiya

It is certified that error appears in the above—identified patent and that said Letters Patent is hereby corrected as shown below:

Column 2, line 68, after "away" insert --from--.

Column 3, line 15, change "theendoscope" to --the endoscope--.

Column 3, line 56, change "part" to --apart--.

Column 4, line 59, change "11" to --111--.

Column 4, line 64, change "designed" to --designated--.

Column 8, line 14, after "includes" delete --/--.

Signed and Sealed this

Twenty-third Day of June 1981

[SEAL]

Attest:

RENE D. TEGTMEYER

Attesting Officer

Acting Commissioner of Patents and Trademarks